US008788051B2

(12) United States Patent
Keuninckx

(10) Patent No.: US 8,788,051 B2
(45) Date of Patent: Jul. 22, 2014

(54) TRANSCUTANEOUS CAPACITIVE DATA LINK

(71) Applicant: Lars Keuninckx, Menchelen (BE)

(72) Inventor: Lars Keuninckx, Menchelen (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/682,685

(22) Filed: Nov. 20, 2012

(65) Prior Publication Data

US 2013/0079847 A1 Mar. 28, 2013

Related U.S. Application Data

(60) Division of application No. 11/482,880, filed on Jul. 10, 2006, now Pat. No. 8,315,705, which is a continuation-in-part of application No. PCT/AU2005/001658, filed on Oct. 28, 2005.

(60) Provisional application No. 60/622,612, filed on Oct. 28, 2004, provisional application No. 60/622,602, filed on Oct. 28, 2004.

(51) Int. Cl.
*A61N 1/00* (2006.01)
(52) U.S. Cl.
USPC .................. 607/57; 607/55; 607/60
(58) Field of Classification Search
USPC ................................ 607/55, 57, 60
See application file for complete search history.

(56) References Cited

U.S. PATENT DOCUMENTS

| 4,400,590 | A | | 8/1983 | Michelson | |
|---|---|---|---|---|---|
| 5,069,210 | A | * | 12/1991 | Jeutter et al. | ..................... 607/57 |
| 5,449,002 | A | | 9/1995 | Goldman | |
| 5,674,264 | A | | 10/1997 | Carter et al. | |
| 5,741,314 | A | | 4/1998 | Daly et al. | |
| 5,906,635 | A | * | 5/1999 | Maniglia | ......................... 607/57 |

(Continued)

FOREIGN PATENT DOCUMENTS

| WO | 01/39569 | 6/2001 |
|---|---|---|
| WO | 01/87014 | 11/2001 |
| WO | 2006/045148 | 5/2006 |

OTHER PUBLICATIONS

Nair, "Human skin as data transmission medium-Skinplex," Newslteer—A House Journal of IEEE Kerala Section, vol. 13, No. 3, Jul.-Sep. 2004. Retrieved from the Internet on Jan. 16, 2006, from URL: http://www.ewh.ieee.org/r10/kerala/jul-Sept_2004.htm.

(Continued)

*Primary Examiner* — Nicole F Lavert
(74) *Attorney, Agent, or Firm* — K&L Gates, LLP

(57) ABSTRACT

An implantable medical device includes a transcutaneous capacitive data link circuit. The link circuit include: a first pair of capacitors each having an external electrode configured to be externally positioned on a recipient and an internal electrode configured to be internally positioned in the recipient; a first voltage driver having positive and negative terminals each connected to one of the external electrodes, and configured to generate a first voltage drive signal responsive to a first input control signal; and a first differential amplifier circuit connected to the internal electrodes, configured to generate a first output data signal representative of the first input control signal.

20 Claims, 3 Drawing Sheets

(56) References Cited

U.S. PATENT DOCUMENTS

| | | | |
|---|---|---|---|
| 5,954,628 A | | 9/1999 | Kennedy |
| 6,035,237 A | * | 3/2000 | Schulman et al. .............. 607/63 |
| 6,161,046 A | | 12/2000 | Maniglia et al. |
| 6,591,139 B2 | | 7/2003 | Loftin et al. |
| 6,700,982 B1 | | 3/2004 | Geurts et al. |
| 6,751,505 B1 | | 6/2004 | van den Honert et al. |
| 6,810,289 B1 | | 10/2004 | Shaquer |
| 8,315,705 B2 | | 11/2012 | Keuninckx |
| 2001/0016678 A1 | | 8/2001 | Kennedy |
| 2003/0158584 A1 | | 8/2003 | Cates et al. |
| 2005/0154428 A1 | | 7/2005 | Bruinsma |

OTHER PUBLICATIONS

Vdovin, et al., "On the possibility of intraocular adaptive optics" Optical Society of America, 2003, vol. 11, No. 7, Apr. 7, 2003, Optics Express, pp. 810-817.

Janapsatya, Januar, "Electronic Communication over the Human Body: A Proof-of-Concept Design Study," Department of Electrical and Computer Engineering, University of Queensland.

International Search Report, PCT/AU2005/001658, Jan. 24, 2006.

Written Opinion of the International Search Report, PCT/AU2005/001658, Jan. 24, 2006.

\* cited by examiner

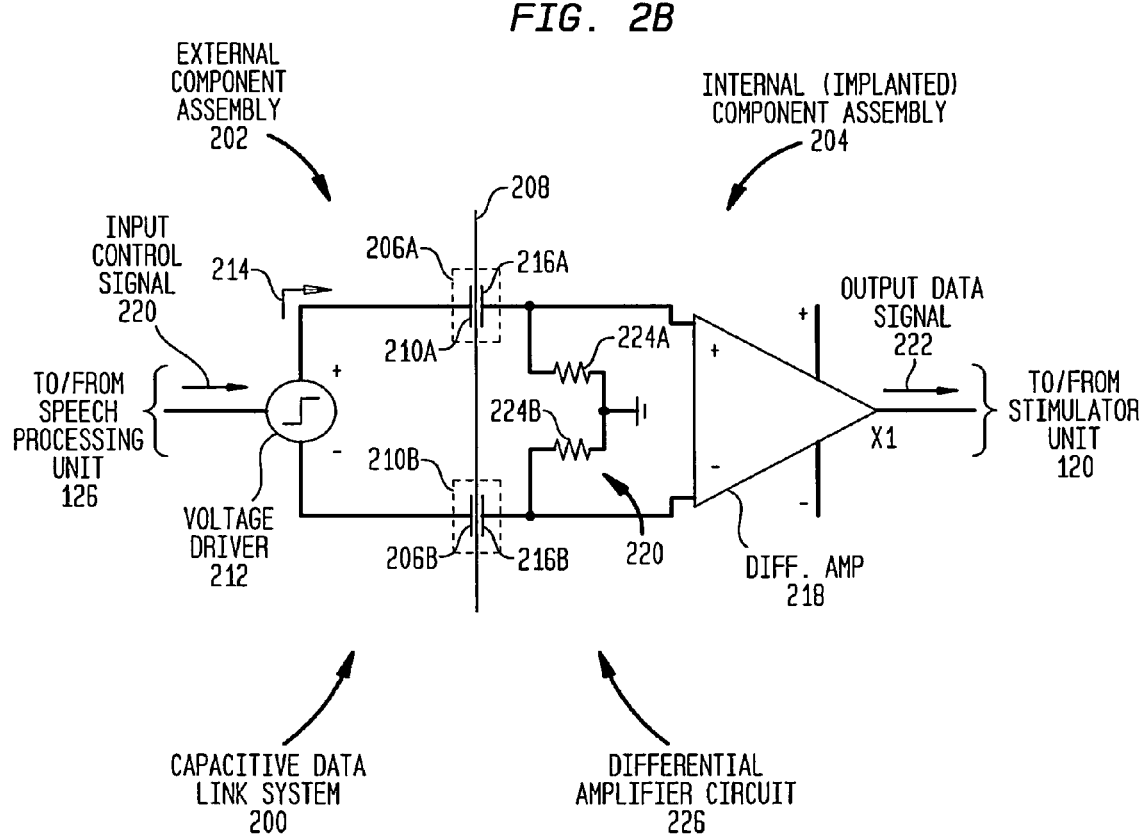

TRANSCUTANEOUS CAPACITIVE DATA LINK

CROSS-REFERENCE TO RELATED APPLICATIONS

This application is a divisional of U.S. application Ser. No. 11/482,880, entitled "Transcutaneous Capacitive Data Link," filed on Jul. 10, 2006, now U.S. Pat. No. 8,315,705, which is a continuation-in-part of International Application No. PCT/AU2005/001658, entitled "Transcutaneous Capacitive Data Link," filed Oct. 28, 2005, now expired, which claims the priority of U.S. Provisional Application No. 60/622,602, entitled "Coupling Out Telemetry Data in a Transcutaneous Transfer System," filed Oct. 28, 2004, and U.S. Provisional Application No. 60/622,612, entitled "Transcutaneous Capacitive Data Link," filed Oct. 28, 2004. The entire disclosure and contents of the above applications are hereby incorporated by reference herein.

This application is related to U.S. patent application Ser. No. 10/883,809, now U.S. Pat. No. 7,171,273, Ser. No. 10/856,823, now U.S. Pat. No. 8,412,341, Ser. No. 10/333,676, now U.S. Pat. No. 7,502,653, Ser. No. 10/887,894, now U.S. Pat. No. 7,860,572 and Ser. No. 10/887,893, now U.S. Pat. No. 8,223,982 and U.S. Pat. Nos. 6,810,289, 6,751,505, and 6,700,982 which are hereby incorporated by reference herein.

BACKGROUND

1. Field of the Invention

The present invention relates generally to transcutaneous transfer systems and, more particularly, to a transcutaneous capacitive data link.

2. Related Art

The use of implantable medical devices to provide therapy to individuals for various medical conditions has become more widespread as the advantages and benefits such devices provide become more widely appreciated and accepted throughout the population. In particular, devices such as hearing aids, implantable pacemakers, defibrillators, functional electrical stimulation devices such as cochlear prostheses, organ assist or replacement devices, and other medical devices, have been successful in performing life saving and/or lifestyle enhancement functions for a number of individuals.

Medical devices often include one or more sensors, processors, controllers or other functional electrical components that are permanently or temporarily implanted in a patient. Many such implantable devices require power and/or require communications with external systems that are part of or operate in conjunction with the medical device. One common approach to provide for the transcutaneous transfer of power and/or communications with an implantable component is via a transcutaneous transfer system.

One type of medical device that may include a transcutaneous transfer system is a Cochlear™ prosthesis (commonly referred to as Cochlear™ prosthetic devices, Cochlear™ implants, Cochlear™ devices, and the like; simply cochlear implant herein.) Cochlear implants provide the benefit of hearing to individuals suffering from severe to profound hearing loss. Hearing loss in such individuals is due to the absence or destruction of the hair cells in the cochlea which transduce acoustic signals into nerve impulses. Cochlear implants essentially simulate the cochlear hair cells by directly delivering electrical stimulation to the auditory nerve fibers. This causes the brain to perceive a hearing sensation resembling the natural hearing sensation normally delivered to the auditory nerve.

Conventional cochlear implants primarily include external components directly or indirectly attached to the body of the patient (sometimes referred to herein as the recipient), and internal components which are implanted in the patient. The external components typically comprise a microphone for detecting sounds, a speech processor that converts the detected sounds into a coded signal, a power source, and an external transmitter antenna coil. The internal components typically comprise an internal receiver antenna coil, a stimulator located within a recess of the temporal bone of the recipient, and an electrode array positioned in the recipient's cochlear.

Collectively, the external transmitter antenna coil and the internal receiver antenna coil form an inductively-coupled transcutaneous transfer system. The external transmitter antenna coil is usually positioned on the side of a recipient's head directly facing the implanted antenna coil to allow for the coupling of the coils to transfer energy and data between the external and internal antenna coils. Typically, the transfer of energy is controlled to effect the transmission of the coded sound signal and power from the external speech processor to the implanted stimulator unit, and to effect the transmission of telemetry data from the implanted stimulator unit to the external speech processor.

SUMMARY

According to one aspect of the present invention, there is provided an implantable medical device, comprising a transcutaneous capacitive data link circuit. The transcutaneous capacitive data link circuit comprises: a first pair of capacitors each having an external electrode configured to be externally positioned on a recipient and an internal electrode configured to be internally positioned in the recipient; a first voltage driver having positive and negative terminals each connected to one of the external electrodes, and configured to generate a first voltage drive signal responsive to a first input control signal; and a first differential amplifier circuit connected to the internal electrodes, configured to generate a first output data signal representative of the first input control signal.

According to another aspect of the present invention, there is a provided an a transcutaneous capacitive data link circuit. The transcutaneous capacitive data link circuit comprises: a first pair of capacitors each having an external electrode configured to be externally positioned on a recipient and an internal electrode configured to be internally positioned in the recipient; first voltage driver means, having positive and negative terminals each connected to one of the external electrodes, for generating a first voltage drive signal responsive to a first input control signal; and first differential amplifier means connected to the internal electrodes, for generating a first output data signal representative of the first input control signal.

According to a yet another aspect of the present invention, there is provided a a transcutaneous capacitive data link circuit is disclosed, the circuit comprising: a first pair of capacitors each having an external electrode configured to be externally positioned on a recipient and an internal electrode configured to be internally positioned in the recipient; a first voltage driver having positive and negative terminals each connected to one of the external electrodes, and configured to generate a first voltage drive signal responsive to a first input control signal; and a first differential amplifier circuit connected to the internal electrodes, configured to generate a first output data signal representative of the first input control signal.

BRIEF DESCRIPTION OF THE DRAWINGS

Embodiments of the present invention are described herein in conjunction with the accompanying drawings, in which:

FIG. 2B is a simplified schematic diagram a capacitive data link in accordance with one embodiment of the present invention.

DETAILED DESCRIPTION

Embodiments of the present invention are directed to the transcutaneous transfer of data using a capacitive link thereby providing for the low-power transmission of data across the skin of a patient without a galvanic connection.

Embodiments of the present invention are described below in connection with one embodiment of an implantable medical device, namely a type of auditory prosthesis commonly referred to as a cochlear implant. As used herein, the term "cochlear implant" refers to any partially- or completely-implantable device that provides electrical stimulation and/or mechanical stimulation to a patient to improve and/or provide hearing sensations. It should be appreciated, however, that the present invention may be implemented in connection with other types of medical implants as well.

Cochlear implants use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a cochlear prosthetic device provides stimulation of the cochlear nucleus in the brainstem.

Figure 1A:
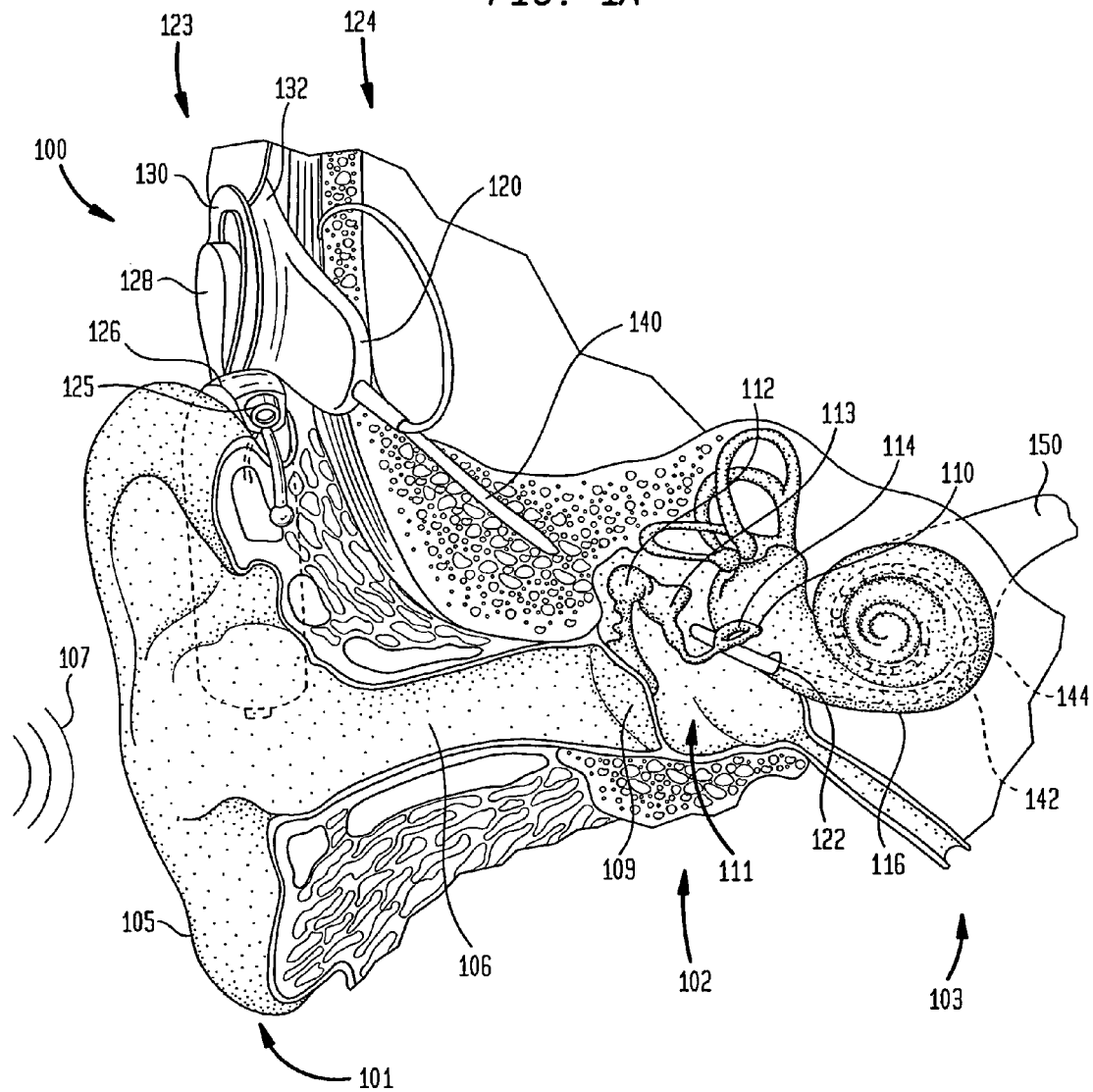
FIG. 1A is a perspective view of internal and external components of a cochlear implant system shown in their operational position on a recipient.

Exemplary cochlear implants in which embodiments of the present invention may be implemented include, but are not limited to, those systems described in U.S. Pat. Nos. 4,532,930, 6,537,200, 6,565,503, 6,575,894 and 6,697,674, which are hereby incorporated by reference herein. A representative example of a cochlear implant is illustrated in FIG. 1. FIG. 1 is a cut-away view of the relevant components of outer ear 101, middle ear 102 and inner ear 103, along with a perspective view of the components of a cochlear implant 100.

In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 109 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 116. Such fluid motion, in turn, activates tiny hair cells (not shown) that line the inside of cochlea 116. Activation of the hair cells causes appropriate nerve impulses to be transferred through the spiral ganglion cells (not shown) and auditory nerve 150 to the brain (not shown), where they are perceived as sound. In deaf persons, there is an absence or destruction of the hair cells. Cochlear implant 100 is needed to directly stimulate the ganglion cells to provide a hearing sensation to the recipient.

FIG. 1 also shows how a cochlear implant 100 is positioned in relation to outer ear 101, middle ear 102 and inner ear 103. Cochlear implant 100 comprises external component assembly 123 which is directly or indirectly attached to the body of the recipient, and an internal component assembly 124 which is temporarily or permanently implanted in the recipient.

External component assembly 123 comprises microphone 125 for detecting sound which is outputted to a BTE (Behind-The-Ear) speech processing unit 126 that generates coded signals and are provided to an external transmitter unit 128, along with power from a power source such as a battery (not shown). External transmitter unit 128 comprises an external coil 130 and, preferably, a magnet (not shown) secured directly or indirectly to the external coil.

Internal component assembly 124 comprises an internal receiver unit 132 having an internal coil (not shown) that receives power and coded signals from external assembly 123. Internal receiver unit 132 transmits the received power and coded signals to a stimulator unit 120 which applies the coded signal to an electrode assembly 144 disposed on the distal end of a carrier member 140. Electrode carrier member 140 enters cochlea 116 at cochleostomy 122 such that one or more electrodes 142 of electrode assembly 144 are aligned with portions of cochlea 116.

Cochlea 116 is tonotopically mapped with each region of the cochlea being responsive to acoustic and/or stimulus signals in a particular frequency range. To accommodate this property of cochlea 116, electrodes 142 are each constructed and arranged to deliver appropriate stimulating signals to particular regions of cochlea 116, each representing a different frequency component of a received audio signal. Signals generated by stimulator unit 120 are applied by the electrodes 142 of electrode array 144 to cochlea 116, thereby stimulating the auditory nerve 150. It should be appreciated that although in the embodiment shown in FIG. 1 electrodes 142 are arranged in array 144, other arrangements are possible.

Figure 2A:
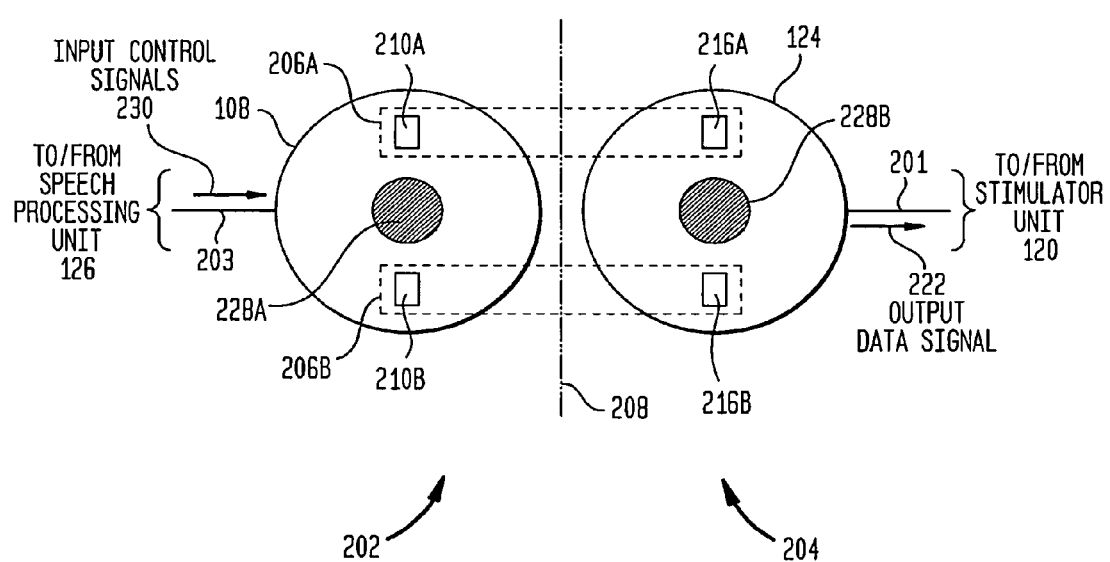
FIG. 2A is a perspective view of an external transmitter unit and an internal receiver unit with external and internal electrodes shown juxtaposed to each other, in accordance with one embodiment of the present invention.

As noted, cochlear implant 100 comprises an embodiment of a capacitive data link system of the present invention to transmit data between internal components 124 and external components 123. A simplified schematic diagram of embodiments of such a capacitive data link system is depicted in FIG. 2A and FIG. 2B. As shown in FIG. 2A, a capacitive data link system 200 comprises external components 202 and internal components 204. External components 204 are worn by the recipient, for example, integrated into speech processor 126 (FIG. 1), or as a separately-worn unit connected to speech processor 126 by a cable. The operational connection to speech processor 126 is generally represented by line 203. Internal components 204 are implanted in the recipient at a location in which a capacitive link may be established, as described herein. Internal components 204 are operatively coupled to stimulator unit 120 (FIG. 1). The operational connection to stimulator unit 120 is generally represented by line 201.

In this exemplary embodiment, capacitive data link system 200 comprises two capacitors 206A and 206B. Each capacitor 206 comprises two electrodes capacitively coupled across skin 208. Specifically, external component assembly 202 comprises an external electrode 210A and 210B of capacitors 206A and 206B, respectively. External component assembly 202 also comprises a voltage driver 212 (FIG. 2B) which generates a biphasic voltage signal 214 to differentially drive external electrodes 210 of capacitors 206 as described herein. Voltage driver 212 is responsive to input control signals 230 generated by speech processing unit 126.

Internal component assembly 204 comprises internal electrodes 216A and 216B of capacitors 206A and 206B, respectively. Each internal electrodes 216A, 216B is connected to one input of a differential amplifier 218 (FIG. 2B) through a resistive network 220. Differential amplifier 218 generates an output data signal 222 which is received by stimulator unit 120 (FIG. 1). Because changes in voltage drive signal 214 are reflected in output data signal 222, speech processing unit 126 may transmit data to stimulator unit 120 by controlling voltage driver 212.

It should be appreciated that the embodiment illustrated in FIG. 2B is a simplified schematic. For example, as one of ordinary skill in the art would appreciated, embodiments of internal component assembly 204 would typically include signal conditioning circuitry to convert output data signal 222 generated by differential amplifier 218 to a form suitable for use by stimulator unit 120 or other internal component 124 of system 100. Such signal conditioning circuitry may include, for example, a comparator, pulse forming circuitry and related circuitry and/or other circuitry to amplify and shape output data signal 222 as required for the particular application.

Capacitors 206A and 206B each comprise oppositely-spaced electrodes 210A/216A and 210B/216B; that is, the opposing electrodes 210, 216 of each capacitor 206 are aligned with each other along an axis line substantially orthogonal to planes defined by the electrodes. Such transcutaneous alignment facilitates the capacitive coupling attained by each capacitor 206 during operation of capacitive data link system 200. In the embodiment shown in FIG. 2A, such alignment is attained by the use of magnets 228A and 228B.

External electrodes 210 are adjacent to and preferably not in contact with skin 208 of the recipient. Accordingly, external electrodes 210 may be encased in a housing formed of a suitable dielectric material. Such housing may provide a desired separation between external electrodes 210 and the recipient and, therefore, between external electrodes 210 and internal electrodes 216.

Internal electrodes 216, on the other hand, are galavanically isolated from the body of the recipient to maintain operational integrity of the device as well as to ensure the device is biocompatible. As such, internal capacitor electrodes 216 may be encapsulated in, for example, a silicon film.

External and internal electrodes 210, 216 may be formed of any conductive material and may have any dimensions suitable for a particular application. For example, in one embodiment, electrodes 210, 216 comprise a conductive material such as copper or platinum metal and are formed as a flexible coil or film. Thus, it should be appreciated that capacitors 206 can be implemented with any conductive material having any dimensions suitable for achieving a capacitive link given the particular patient and where on the patient the capacitor is located. It should also be appreciated that the materials used to form the external electrode of a capacitor 206 need not be the same as the materials used to form the internal electrode of that same capacitor 206.

Preferably, external electrode 210 and internal electrode 216 of each electrode 206 have the substantially the same dimensions and surface area. In addition, in many embodiments, capacitors 206 are as large as possible to facilitate signal coupling, while taking into consideration the limits imposed on capacitor size due to the size of the recipient's head, the distance between opposing electrodes 210, 216 of each capacitor 206, etc. In one embodiment, electrodes 210, 216 are rectangular and have a surface area of approximately 1 cm$^3$. It should be appreciated, then, that the surface area and dimensions of electrodes 210, 216 may vary depending on the requirements of the particular application.

As one of ordinary skill in the art would appreciate, the capacitance of each capacitor 206 is determined by a number of factors such as the dimensions and spacing of its electrodes 210, 216, and the material, here, skin and perhaps hair, between the electrodes of the capacitor. In some embodiments in which capacitors 206 are designed for use in connection with a cochlear implant system such as system 100 introduced above, the capacitance of each capacitor 206 is in the range of approximately 0.1 pf-0.5 pf. In alternative embodiments implemented in connection with the same or different application, the capacitance of each capacitor 206 may be different, and based on a variety of factors including the distance and material between electrodes 210, 216.

As noted, external components 202 include a voltage driver 212. Voltage driver 212 generates differential voltage signal 214 to generate an electric field change on internal electrodes 216 of capacitors 206. Preferably voltage driver 212 generates a pulse waveform, although any biphasic waveform such as a sinusoidal waveform may be used to differentially drive capacitors 206. In one embodiment, voltage driver 212 generates a 5 volt signal for the implemented TTL circuitry. It should be appreciated, however, that any suitable voltage signal generated by any voltage source now or later developed can be used in alternative embodiments. For example, in one alternative embodiment, voltage driver 212 generates a 3 volt signal.

In one embodiment, capacitive data link system 200 is powered, for example, by a battery. In such embodiments, the amplitude of voltage signal 214 may be limited. In alternative embodiments, a voltage signal 214 with relatively greater amplitude may be provided to support greater signal strength. As one of ordinary skill in the art would appreciate, such a voltage boost will likely consume additional power and, therefore require some trade-offs.

As noted, internal electrodes 216 of capacitors 206 are connected to respective inputs of a discrete differential amplifier 218 through a resistive network 220. Differential amplifier 218 amplifies the difference in electric potential between the two inputs. In this way, common mode variations caused not by external sources are substantially isolated. Preferably, differential amplifier 218 is a transistor differential amplifier implementing JFETs due to its high input resistance and low input capacitance. As one of ordinary skill in the art would appreciate, differential amplifier 218 may be implemented in a variety of ways with a variety of components well known in the art.

Resistive network 220 is provided to adjust the input impedance of differential amplifier 218. In one embodiment, resistors 224A and 224B are approximately 1 MOhm. It should be appreciated that the values of resistors 224 may be selected based on conventional design considerations well-known to those of ordinary skill in the art. In the above exemplary embodiment, the resulting differential voltage across the inputs of amplifier 218 is approximately 20 mV. Collectively, differential amplifier 218 and resistive network 220 are referred to herein as differential amplifier circuit 226.

As understood by those of ordinary skill in the art, the current through capacitors 206 is determined by the rise time and the height of voltage signal 214 generated by voltage driver 212. This also determines the amplitude of output data signal 222. The current through capacitors 206 is also proportional to the size of electrodes 206. As such, the voltage provided to the inputs of differential amplifier 218 is approximately proportional to its input impedance and this current.

It should also be appreciated that just a few embodiments of the present invention have been described herein. For example, although capacitive data link system 200 is herein described as having components that are internal or external to the patient, it should be understood that in another embodiment of the present invention, the capacitive data link system may be configured to also have components 202 internal to the patient, and having components 204 external to the patient, to permit bi-directional communication. A bi-directional half duplex data link may be achieved, for example, with the addition of a multiplexer and additional driver and receiver components. One advantage of such embodiments is that bi-directional communication of data can be achieved with low power usage. It should be appreciated that such bi-directional communication can be half-duplex or full-duplex.

The present invention advantageously allows for the functional separation of data and power transmission, enabling each to be optimally configured without concern for the potential adverse effects on the other type of transmission. In one embodiment of the present invention, the data rate is approximately 1 megabit per second, or 1 megahertz. It should be appreciated, however, that the data rate can be significantly higher or lower should a different data bandwidth be required.

One advantage of certain embodiments of the present invention is that high data transmission rates can be achieved with low power usage. In one embodiment for example, the transmission rate is 1 MHz. It should be appreciated, however, that the transmission rate is determined by a number of factors including, but not limited to, the skin and the hair that are located between the external and internal plates of each capacitor 206.

Yet another advantage of certain embodiments of the present invention is that longer data streams can be achieved with low power usage, than is possible where energy and data transfers are transmitted through a combined means.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An implantable medical device, comprising:
a transcutaneous capacitive data link circuit comprising:
a first pair of capacitors each having an external electrode configured to be externally positioned on a recipient and an internal electrode configured to be internally positioned in the recipient;
a first voltage driver having positive and negative terminals each connected to one of the external electrodes, and configured to generate a first voltage drive signal responsive to a first input control signal; and
a first differential amplifier circuit connected to the internal electrodes, configured to generate a first output data signal representative of the first input control signal.

2. The implantable medical device of claim 1, wherein the data link circuit further comprises:
a second pair of capacitors each having an external electrode configured to be externally positioned on a recipient and an internal electrode configured to be internally positioned in the recipient;
a second voltage driver having positive and negative terminals each connected to one of the internal electrodes of the second pair of capacitors, and configured to generate a second voltage drive signal responsive to a second input control signal; and
a second differential amplifier circuit connected to the external electrodes of the second pair of capacitors, configured to generate a second output data signal representative of the second input control signal.

3. The implantable medical device of claim 2, wherein:
the second input control signal comprises telemetry signals generated by an implanted stimulator unit of the implantable medical device; and
the second output data signal is suitable for receipt by a speech processor unit of the implantable medical device.

4. The circuit of claim 2, wherein the second differential amplifier circuit comprises:
a differential amplifier; and
a resistive network connected between the differential amplifier and the internal electrodes.

5. The implantable medical device of claim 1, wherein:
the first input control signal comprises a coded sound signal generated by a speech processor unit of an implantable medical device, and
the first output control signal is suitable for receipt by an implanted stimulator unit of the implantable medical device.

6. The implantable medical device of claim 1, wherein the first differential amplifier circuit comprises:
a differential amplifier; and
a resistive network connected between the differential amplifier and the internal electrodes.

7. The implantable medical device of claim 1, wherein:
each capacitor of the first pair thereof includes opposing electrodes;
each electrode is substantially planar and has an axis substantially orthogonal thereto; and
for each capacitor, the axes of opposing electrodes thereof are substantially aligned with each other.

8. The implantable medical device of claim 1, wherein:
the implantable medical device is an implantable auditory prosthesis.

9. The implantable medical device of claim 8, wherein:
the implantable auditory prosthesis is a cochlear implant.

10. An implantable medical device, comprising:
a transcutaneous capacitive data link circuit comprising:
a first pair of capacitors each having an external electrode configured to be externally positioned on a recipient and an internal electrode configured to be internally positioned in the recipient;
first voltage driver means, having positive and negative terminals each connected to one of the external electrodes, for generating a first voltage drive signal responsive to a first input control signal; and
first differential amplifier means connected to the internal electrodes, for generating a first output data signal representative of the first input control signal.

11. The implantable medical device of claim 10, wherein the data link circuit further comprises:
a second pair of capacitors each having an external electrode configured to be externally positioned on a recipient and an internal electrode configured to be internally positioned in the recipient;

second voltage driver means having positive and negative terminals each connected to one of the internal electrodes of the second pair of capacitors, for generating a second voltage drive signal responsive to a second input control signal; and second differential amplifier means connected to the external electrodes of the second pair of capacitors, for generating a second output data signal representative of the second input control signal.

12. The implantable medical device of claim 11, wherein:
the second input control signal comprises telemetry signals generated by an implanted stimulator unit of an implantable medical device, and
the second output data signal is suitable for receipt by a speech processor unit of the implantable medical device.

13. The implantable medical device of claim 10, wherein:
the first input control signal comprises a coded sound signal generated by a speech processor unit of an implantable medical device, and
the first output control signal is suitable for receipt by an implanted stimulator unit of the implantable medical device.

14. A transcutaneous capacitive data link circuit comprising:
a first pair of capacitors each having an external electrode configured to be externally positioned on a recipient and an internal electrode configured to be internally positioned in the recipient;
a first voltage driver having positive and negative terminals each connected to one of the external electrodes, and configured to generate a first voltage drive signal responsive to a first input control signal; and
a first differential amplifier circuit connected to the internal electrodes, configured to generate a first output data signal representative of the first input control signal.

15. The circuit of claim 14, further comprising:
a second pair of capacitors each having an external electrode configured to be externally positioned on a recipient and an internal electrode configured to be internally positioned in the recipient;
a second voltage driver having positive and negative terminals each connected to one of the internal electrodes of the second pair of capacitors, and configured to generate a second voltage drive signal responsive to a second input control signal; and
a second differential amplifier circuit connected to the external electrodes of the second pair of capacitors, configured to generate a second output data signal representative of the second input control signal.

16. The circuit of claim 15, wherein:
the second input control signal comprises telemetry signals generated by an implanted stimulator unit of a cochlear implant; and
the second output data signal is suitable for receipt by a speech processor unit of the cochlear implant.

17. The circuit of claim 15, wherein the second differential amplifier circuit comprises:
a differential amplifier; and
a resistive network connected between the differential amplifier and the internal electrodes.

18. The circuit of claim 14, wherein:
the first input control signal comprises a coded sound signal generated by a speech processor unit of a cochlear implant; and
the first output control signal is suitable for receipt by an implanted stimulator unit of the cochlear implant.

19. The circuit of claim 14, wherein the first differential amplifier circuit comprises:
a differential amplifier; and
a resistive network connected between the differential amplifier and the internal electrodes.

20. The circuit of claim 14, wherein:
each capacitor of the first pair thereof includes opposing electrodes;
each electrode is substantially planar and has an axis substantially orthogonal thereto; and
for each capacitor, the axes of opposing electrodes thereof are substantially aligned with each other.

* * * * *